(12) United States Patent
van Zonneveld et al.

(10) Patent No.: US 6,447,768 B1
(45) Date of Patent: Sep. 10, 2002

(54) METHODS OF GENE THERAPY WITH A DNA SEQUENCE ENCODING NOS

(75) Inventors: Anton Jan van Zonneveld, Herent (BE); Stefan Frederik Franciscus Verlingen, Leiden (NL)

(73) Assignee: Introgene B.V., Leiden (NL)

( * ) Notice: Subject to any disclaimer, the term of this patent is extended or adjusted under 35 U.S.C. 154(b) by 0 days.

(21) Appl. No.: 09/474,178

(22) Filed: Dec. 29, 1999

(30) Foreign Application Priority Data

Dec. 30, 1998 (EP) .............................. 98204482

(51) Int. Cl.[7] .................. A01N 63/00; A01N 43/04; A61K 48/00; A61K 31/70; C12N 15/00
(52) U.S. Cl. .................. 424/93.2; 424/93.6; 514/44; 435/320.1; 435/325; 435/366; 435/455
(58) Field of Search .................. 514/44; 424/93.2, 424/93.6; 435/325, 455, 320.1

(56) References Cited

U.S. PATENT DOCUMENTS 5,436,146 A * 7/1995 Shenk et al. ............. 435/172.3

FOREIGN PATENT DOCUMENTS

| WO | WO 94/28152 | * 12/1994 | ........... C12N/15/86 |
| WO | WO 96/20276 | * 7/1996 | ........... C12N/15/11 |
| WO | WO 97/00326 | * 7/1996 | ........... C12N/15/86 |

OTHER PUBLICATIONS

Channon et al (1996) Cardiovascular Res. 32, 962–972.*
Shears et al (1997) Japanese J. Pharm. 75, p. 18P, abs. 62.*
Janssens et al (1996) J. Clinc. Invest. 98, 317–324.*
Mackey et al (1979) J. Virol. 29, 1056–1064.*
Anderson (1998) Nature 392, 25–30.*
Ross et al (1996) Human Gene Therapy 7, 1781–1790.*
Fallaux et al., "New Helper Cells and Matched Early Region 1–Deleted Adenovirus Vectors Prevent Generation of Replication–Competent Adenoviruses", *Human Gene Therapy*, 9:1909–1917, Sep. 1, 1998.
Janssens et al., "Human Endothelial Nitric Oxide Synthase Gene Transfer Inhibits Vascular Smooth Muscle Cell Proliferation and Neointima Formation After Balloon Injury in Rats", *Circulation*, pp. 1274–1281, Apr. 7, 1998.
Laitinen et al., "Vascular gene transfer for the treatment of restenosis and atherosclerosis", *Current Opinion in Lipidology*, pp. 465–469, Oct. 1998.
Partial European Search Report, EP 98 20 4482, dated Aug. 23, 1999, 5 pages.
Shears et al., "Efficient Inhibition of Intimal Hyperplasia by Adenovirus–Mediated Inducible Nitric Oxide Synthase Gene Transfer to Rats and Pigs In Vivo", *Journal of the American College of Surgeons*, vol. 187, No. 3, pp. 295–306, Sep. 1998.
Witzenbichler et al., "Vascular Endothelial Growth factor–C (VEGF–C/VEGF–2) Promotes Angiogenesis in the Setting of Tissue Ischemia", *American Journal of Pathology*, vol. 153, No. 2, pp. 381–394, Aug. 1998.

* cited by examiner

*Primary Examiner*—Deborah Crouch
(74) *Attorney, Agent, or Firm*—TraskBritt

(57) ABSTRACT

A nucleic acid delivery vehicle for enhancing and/or inducing angiogenesis. This nucleic acid delivery vehicle includes a nucleic acid having at least one sequence coding for a protein capable of increasing nitric oxide production, and further includes a nucleic acid delivery carrier. The vehicle can be used in a method for enhancing and/or inducing angiogenesis in an individual which involves providing cells of the individual with the nucleic acid delivery vehicle. Also disclosed is a cell for producing the nucleic acid delivery vehicle for enhancing and/or inducing angiogenesis. As before, the nucleic acid delivery vehicle includes a nucleic acid having at least one sequence coding for a protein capable of increasing nitric oxide production, and further includes a nucleic acid delivery carrier wherein the nucleic acid delivery carrier includes a virus vector selected from the group of adenoviral vector and adeno-associated viral vectors, the cell comprising means for producing the virus vector in the absence of replication competent adenovirus and adeno-associated virus.

11 Claims, 5 Drawing Sheets

SEQUENCE LISTING

<160> NUMBER OF SEQ ID NOS: 29

<210> SEQ ID NO 1
<211> LENGTH: 21
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 1
gcctcatgaa ctttctgctg t                                              21

<210> SEQ ID NO 2
<211> LENGTH: 51
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 2
cccctcgagt ctagatcacc gcctcggctt gtcacatttt tcttgtcttg c              51

<210> SEQ ID NO 3
<211> LENGTH: 21
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 3
ggcacatgtc ggggcccggg a                                              21

<210> SEQ ID NO 4
<211> LENGTH: 36
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 4
cccctcgagt ctagatcaca gcctggggag gaagtg                              36

<210> SEQ ID NO 5
<211> LENGTH: 35
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 5
cgggatccgc caccatggcc agtcgggaag aggag                               35

<210> SEQ ID NO 6
<211> LENGTH: 33
<212> TYPE: DNA
<213> ORGANISM: Unknown Organism
<220> FEATURE:
<223> OTHER INFORMATION: Description of Unknown Organism:Relating to
      Field of Human Gene Therapy

```
<400> SEQUENCE: 6
cggaattctt aaaaatcaaa ggggttctgc cgc                           33

<210> SEQ ID NO 7
<211> LENGTH: 23
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 7
aattgtctta attaaccgct taa                                     23

<210> SEQ ID NO 8
<211> LENGTH: 19
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 8
aattgtctta attaaccgc                                          19

<210> SEQ ID NO 9
<211> LENGTH: 19
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 9
aattgcggtt aattaagac                                          19

<210> SEQ ID NO 10
<211> LENGTH: 23
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 10
ggcgtacgta gccctgtcga aag                                     23

<210> SEQ ID NO 11
<211> LENGTH: 27
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 11
ccaatgcatt cgaagtactt ccttctc                                 27

<210> SEQ ID NO 12
<211> LENGTH: 22
<212> TYPE: DNA
<213> ORGANISM: Unknown Organism
<220> FEATURE:
<223> OTHER INFORMATION: Description of Unknown Organism:Relating to
      Field of Human Gene Therapy
```

```
<400> SEQUENCE: 12
ccaatgcata cggcgcagac gg                                              22

<210> SEQ ID NO 13
<211> LENGTH: 21
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 13
gagctggatc ccatggacga g                                               21

<210> SEQ ID NO 14
<211> LENGTH: 27
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 14
gggggatccg aacttgttta ttgcagc                                         27

<210> SEQ ID NO 15
<211> LENGTH: 25
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 15
gggagatcta gacatgataa gatac                                           25

<210> SEQ ID NO 16
<211> LENGTH: 27
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 16
gggagatctg tactgaaatg tgtgggc                                         27

<210> SEQ ID NO 17
<211> LENGTH: 24
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 17
ggaggctgca gtctccaacg gcgt                                            24

<210> SEQ ID NO 18
<211> LENGTH: 47
<212> TYPE: DNA
<213> ORGANISM: Unknown Organism
<220> FEATURE:
<223> OTHER INFORMATION: Description of Unknown Organism:Relating to
      Field of Human Gene Therapy
```

```
<400> SEQUENCE: 18
ctgtacgtac cagtgcactg gcctaggcat ggaaaaatac ataactg                    47

<210> SEQ ID NO 19
<211> LENGTH: 64
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 19
gcggatcctt cgaaccatgg taagcttggt accgctagcg ttaaccgggc gactcagtca      60
atcg                                                                  64

<210> SEQ ID NO 20
<211> LENGTH: 27
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 20
gcgccaccat gggcagagcg atggtgg                                         27

<210> SEQ ID NO 21
<211> LENGTH: 50
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 21
gttagatcta agcttgtcga catcgatcta ctaacagtag agatgtagaa                50

<210> SEQ ID NO 22
<211> LENGTH: 67
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 22
gccatcccta ggaagcttgg taccggtgaa ttcgctagcg ttaacggatc ctctagacga     60
gatctgg                                                               67

<210> SEQ ID NO 23
<211> LENGTH: 67
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 23
ccagatctcg tctagaggat ccgttaacgc tagcgaattc accggtacca agcttcctag     60
ggatggc                                                               67
```

```
<210> SEQ ID NO 24
<211> LENGTH: 39
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 24
gatcggtacc actgcagtgg tcaatattgg ccattagcc                            39

<210> SEQ ID NO 25
<211> LENGTH: 29
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 25
gatcaagctt ccaatgcacc gttcccggc                                       29

<210> SEQ ID NO 26
<211> LENGTH: 21
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 26
gggtattagg ccaaaggcgc a                                               21

<210> SEQ ID NO 27
<211> LENGTH: 33
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 27
gatcccatgg aagcttgggt ggcgacccca gcg                                  33

<210> SEQ ID NO 28
<211> LENGTH: 36
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 28
gatcccatgg ggatccttta ctaagttaca aagcta                               36

<210> SEQ ID NO 29
<211> LENGTH: 19
<212> TYPE: DNA
<213> ORGANISM: Unknown Organism
<220> FEATURE:
<223> OTHER INFORMATION: Description of Unknown Organism:Relating to
      Field of Human Gene Therapy

<400> SEQUENCE: 29
gtcgctgtag ttggactgg                                                  19
```

METHODS OF GENE THERAPY WITH A DNA SEQUENCE ENCODING NOS

FIELD OF THE INVENTION

The present invention relates to the field of human gene therapy, more in particular to gene therapy vehicles for the treatment of cardiovascular disease.

BACKGROUND OF THE INVENTION

Hypertension and hypercholesterolemia are two of the main risk factors for human health in the Western world; these conditions can lead to atherosclerosis. Atherosclerosis may result in a number of severe cardiovascular diseases, like chronic heart failure, angina pectoris, claudicatio intermittens, or peripheral and myocardial ischemia. At least the early phases of atherosclerosis are characterised by endothelial dysfunction. Endothelial dysfunction causes coronary arterial construction, plays a role in both hypertension and hypercholesterolemia. It is one of the first measurable steps in the cascade of reactions leading to atherosclerosis, even before macroscopic lesions are evident. Many therapies have been investigated to assess the possibility to reverse the endothelial dysfunction, and to stimulate the formation of new blood vessels (angiogenesis). It has been suggested that oral L-arginine supplementation in the diet may be a therapeutic strategy to improve angiogenesis in patients with endothelial dysfunction.

It is well established that angiogenesis is mediated by a multitude of cytokines (like TNF-α and E-selectin) and angiogenic factors including bFGF (basic Fibroblast Growth Factor), VEGF (Vascular Endothelial Growth Factor), and TGF-β. Both bFGF and VEGF are key regulators of angiogenesis in adult tissues. They selectively stimulate proliferation of endothelial cells, starting with the binding of these growth factors to receptors present on the endothelial cell surface. Nitric oxide (NO) has been shown to play a role in this process. NO, originally identified as endothelium-derived relaxing factor, is an important endothelial vasoactive factor.

While both NO and angiogenic factors like bFGF and VEGF play a key role in the endothelial functions, their precise mode of action is not known. On the one hand, levels of angiogenic factors like bFGF and VEGF are increased in patients suffering from endothelial dysfunction. On the other hand, is the release of nitric oxide in vascular endothelial dysfunction often reduced. This reduced release may cause constriction of the coronary arteries and thus contribute to heart disease. It is postulated that patients suffering from endothelial dysfunction could benefit from therapies to increase new collateral blood vessel formation and/or therapies to increase vasodilation.

Many experimental gene therapies concentrate on the stimulation of angiogenesis, in patients suffering from endothelial dysfunction, through the addition of VGEF or bFGF. Though these experimental therapies may have some effect, the level of therapy induced angiogenesis is low, leading to a slow, if at all, recovery or enhancement of blood flow.

It has been demonstrated that NO is involved in VEGF-mediated proliferation of endothelial cells. Exposure of endothelial cells to VEGF was shown to lead to the activation of constitutive NO synthase (ceNOS) and the release of biologically active NO. The proliferation of cells by VEGF can be inhibited by specific NOS-inhibitors like L-NAME, indicating that NO is an essential mediator in the VEGF-induced cell proliferation and angiogenesis.

Likewise, the presence of bFGF can increase ceNOS protein levels and enzyme activity during healing of rat gastric ulcers. Here also, the healing was inhibited specifically by the NOS-inhibitor L-NAME. In transgenic mouse models, disruption of the endogenous ceNOS gene impaired angiogenesis (Murohara et al.). This could not be compensated by the administration of VEGF, showing the essential role for NO in growth factor mediated angiogenesis.

SUMMARY OF THE INVENTION

The art teaches that NO is a secondary signal in the angiogenic response of endothelial cells to growth factors like bFGF and VEGF, and that NO acts as a downstream mediator of angiogenesis. Furthermore, the art suggest that the expression of the ceNOS gene in endothelial cells is a result of the induction by the growth factors, leading to the release of biologically active NO.

However, despite the increase in the levels of angiogenic factors like bFGF and VEGF, this does not result in sufficient collateral forming capacity.

In one aspect of the present invention we demonstrate that at least one of the limiting factors is NO. In another aspect of the invention we demonstrate that NO levels in the arterial wall are insufficient. In another aspect the invention provides a method for increasing angiogenesis through locally increasing NO and/or endothelial growth factors such as but not limited to VGEF and/or bFGF. In yet another aspect of the invention provides a method for increasing vasodilation of blood vessels. In another aspect the invention provides a method for increasing angiogenesis through locally delivering an expression vector, preferably an adenovirus vector, comprising at least an expression cassette for ceNOS, to sites selected for being provided with the capacity to induce, or at least in part promote, angiogenesis.

DETAILED DESCRIPTION OF THE INVENTION

Figure 1:
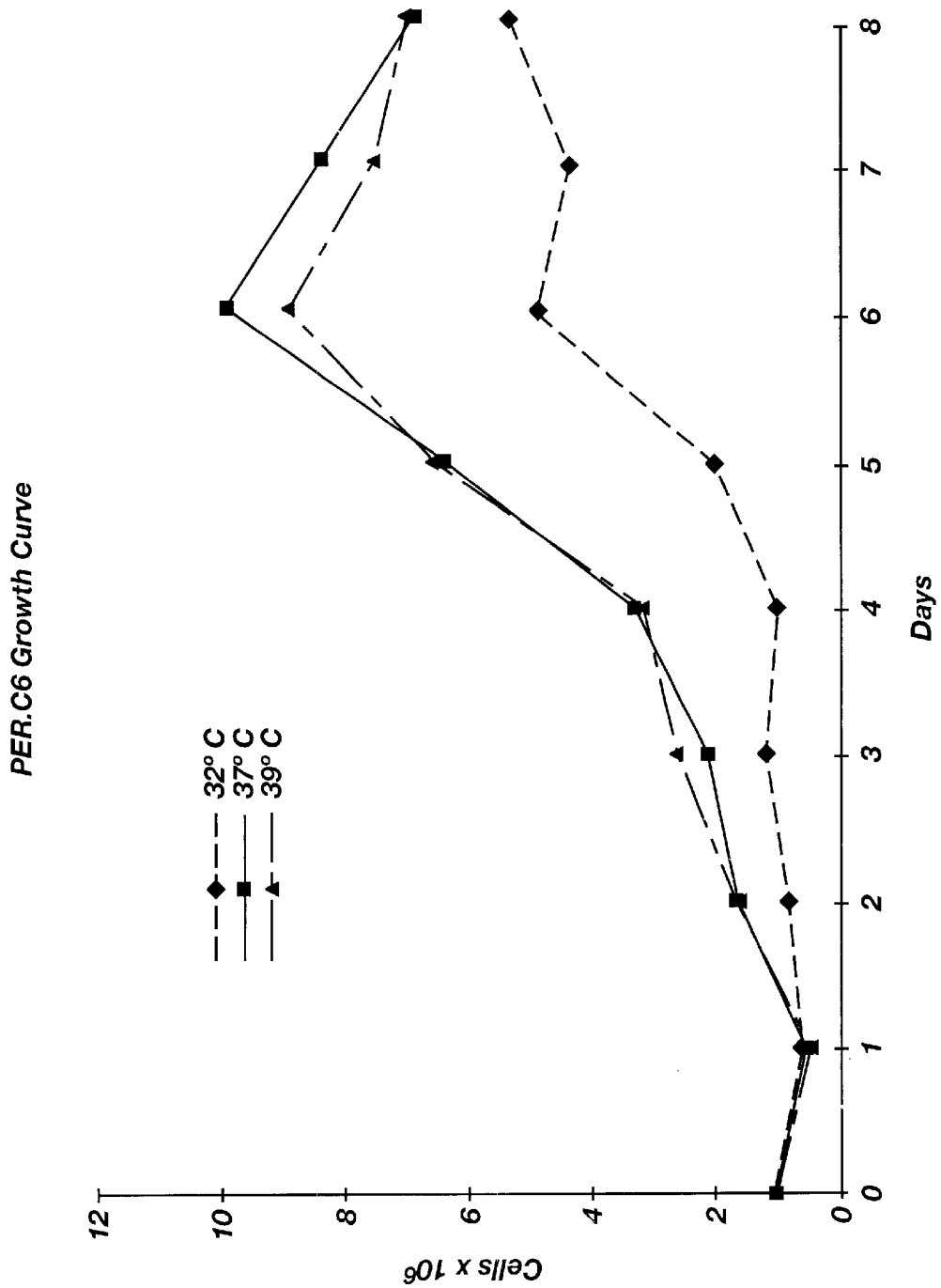
FIG. 1. Cell number of cultures of PER.C6 cells grown at 32, 37 or 39 degrees centigrade.

A rationale for the present invention is provided by the observation that the formation of new blood vessels in vitro cultures of human foreskin microvascular endothelial cells (MVEC) was increased through providing said cells with a sequence coding for a VGEF, a bFGF or a nitric oxide synthetase. Moreover, a surprisingly synergistic effect of the combination of a sequence coding for a nitric oxide synthetase with a sequence encoding other angiogenesis promoting factors such as VGEF, bFGF was found. This effect was unanticipated because nitric oxide is produced as a result of the exposure of endothelial cells to VGEF and/or bFGF. Since these factors promote the production of NO a lower than additional effect of extra NO was expected. One possible explanation for the observed synergistic effect is that the signal for stimulation and/or enhancement of angiogenesis by VGEF and/or bFGF triggers at least two signal transduction pathways. In at least one pathway NO is at least in part involved in continuing and/or amplifying the signal cascade, whereas in at least one other pathway, NO is not essentially involved. Both the NO comprising and the NO "independent" signal transduction pathway need to function optimally for optimal induction and/or enhancement of angiogenesis. In case of the presence of only NO, the NO "independent" is not optimally induced, whereas in case of the presence of only VGEF and/or bFGF, the NO comprising signal transduction pathway is not optimally induced. It is not known whether said pathway are completely separate. It may be that said pathways are separate in a certain part of the cascade and may join together in another part or parts of signal transduction cascade.

In one aspect the invention provides a nucleic acid delivery vehicle for enhancing and/or inducing angiogenesis comprising nucleic acid comprising at least one sequence coding for a protein capable of increasing nitric oxide production and further comprising a nucleic acid delivery carrier. Preferably said sequence codes for a nitric oxide synthetase. Preferably said sequences codes for ceNOS. In a preferred embodiment said nucleic acid delivery vehicle further comprises at least one sequence encoding an additional angiogenesis promoting factor. Preferably said additional angiogenesis promoting factor is of VGEF, bFGF or angiopoietin-1 or parts or derivatives or functional analogues thereof. Said additional angiogenesis promoting factors, necessary for obtaining a synergistic effect may be supplied by sequences provided by said nucleic acid delivery vehicle or be provided in other ways. They may also be provided by cells transduced or surrounding transduced cells. In a preferred embodiment of the invention the expression of at least one of said sequences is regulated by a signal. Preferably the signal is provided by the oxygen tension in a cell. Preferably said oxygen tension signal is translated into a different expression by a hypoxia inducible factor 1α promoter.

In another aspect of the invention the nucleic acid delivery vehicle further comprising a sequence encoding a herpes simplex virus thymidine kinase. Thus providing an additional method of regulating the level of enhanced and/or induced angiogenesis. The level may be at least in part be reduced through the addition of gancyclovir, killing not only at least in part the dividing cells in the newly forming vessel parts, but also killing at least in part transduced cells thereby limiting the supply of nitric oxide and/or additionally angiogenesis promoting factors.

The nucleic acid delivery carrier may be any nucleic acid delivery carrier. In a preferred embodiment of the invention the nucleic acid delivery carrier comprises an adenovirus vector or an adeno-associated virus vector preferably including at least essential parts of adenovirus vector DNA or adeno-associated virus vector DNA. Preferably a nucleic acid delivery vehicle has been provided with a least a partial tissue tropism for muscle cells. Preferably a nucleic acid delivery vehicle has been at least in part deprived of a tissue tropism for liver cells. Preferably the tissue tropism is provided or deprived at least in part through a tissue tropism determining part of fiber protein of a subgroup B adenovirus. A preferred subgroup B adenovirus is adenovirus 16.

In another aspect the invention provides a method for enhancing and/or inducing angiogenesis comprising providing cells of an individual with a nucleic acid delivery vehicle according to the invention and allowing the cells to grow under conditions allowing expression of a protein capable of increasing nitric oxide production. Preferably the method is a method for enhancing and/or inducing angiogenesis in a synergistic fashion with at least one additional angiogenesis promoting factor or parts or derivatives or functional analogues thereof. Preferably the enhancing and/or inducing angiogenesis effect is at least in part reversible. Preferably, the effect is at least in part revered though an increase in the oxygen tension or through providing the cells with gancyclovir or functional analogue thereof, or both.

In a preferred aspect of the invention, cells are transduced that, under normal circumstances, are not in direct contact with blood. The advantage being that in this way the treatment promotes at least in part the localisation of the effect. Preferably, the cells not in direct contact with the blood are muscle cells, preferably smooth muscle cells. When feasible it a preferred means of providing cells with a nucleic acid delivery vehicle of the invention is a catheter, preferably an Infiltrator catheter (EP 97200330.5) In one aspect, the invention provides the use of a nucleic acid delivery vehicle or a method for the treatment of endothelial dysfunction. In one embodiment, the use increases at least in part vasodilation of constricted vessels. In another embodiment, the use increases at least in part angiogenesis, be it enhanced or induced or both.

In another aspect the invention provides a cell for the production of an adenovirus vector or an adneo-associated virus vector of the invention wherein said cell comprises a means for the production of said virus vector in the absence of replication competent adenovirus and adeno-associated virus. In a preferred embodiment, the cell expresses at least one means for the production of the virus vector from a nucleic acid integrated in the chromosomal DNA of the cell and expresses other means for the production of said virus vector from nucleic acid not integrated in the chromosomal DNA of the cell and wherein the integrated nucleic acid and the non-integrated nucleic acid, do not comprise sequence overlap leading to the formation of replication competent adenovirus. In a particularly preferred embodiment, the integrated nucleic acid comprises at least an adenovirus E1-region. In another particularly preferred embodiment the integrated nucleic acid comprises at least a sequence encoding an adenovirus E2A protein, preferably an E2A-protein derived from adenovirus ts125. In another preferred embodiment the integrated nucleic acid comprises an adenovirus E4-region, preferably E4-orf6. Preferably the cell is derived from a PER.C6 cell (ECACC deposit number 96022940).

The invention provides gene therapies for local administration of NO or VEGF in the arterial wall. The invention acts to induce angiogenesis in patients with endothelial dysfunction. Furthermore, the invention provides to provide methods to increase NO production in the endothelium, thereby removing a cause for endothelial dysfunction. Gene therapy vehicles and methods of application are disclosed herein, based on the expression in endothelial cells of a NO synthase sequence, along or in combination with sequences encoding angiogenic factors like bFGF or VEGF. The synthesis of NO synthase is regulated by a family of isozymes. Three isoforms are known, nNOS, ceNOS and iNOS. Both nNOS and ceNOS are constitutively expressed and tightly regulated by calmodulin, whereas iNOS is induced by the action of cytokines.

The present invention includes the treatment of human microvascular endothelial cells with VEGF or bFGF, resulting in capillary blood vessel formation. The invention also includes the transfection of these cells with a NOS sequence, resulting in a strong response in capillary vessel formation.

Furthermore, the invention includes the treatment with combinations of sequences encoding NO synthase and VEGF or bFGF, resulting in a strong synergistic response in angiogenesis.

The invention provides viral vectors that contain a nitric oxide synthase (NOS) sequence, or a sequence encoding bFGF or VEGF, or combinations of these. Such viral vectors are useful in gene therapy strategies aimed at improving angiogenesis in patients with impaired endothelial function. In an embodiment of the invention, adenoviral vectors are employed to deliver these sequences. Adenoviruses are convenient viruses for construction of vectors for gene therapy, because of their high efficacy to deliver DNA in most mammalian cell types. Based on the detailed knowledge of their DNA genomes, especially of adenovirus types 2 and 5, recombinant adenoviral vectors have been developed (Bout review, 1997). The recombinant adenoviruses lack E1 sequences to prohibit replication; the recombinant virus may also carry deletion of all E2A sequences. In the present invention, vectors are provided that lack both E1 and E2A sequences, where these sequences have been replaced with either a nitric oxide synthase (NOS) transgene, a transgene encoding bFGF or VEGF, or combinations of these transgenes.

In a further embodiment of the present invention, adenoviral vectors are provided that lack the early genes E1 and E2A, the sequences of which are replaced by the transgenes. In another embodiment of the present invention, complementing cell lines are provided for packaging of such adenoviral vectors.

It is to be understood that when reference is made to a certain protein, that for the purpose of the invention also functional analogues or derivatives of said protein may be used, wherein said functional analogue possesses the same kind of activity though not necessarily the same amount of activity.

EXAMPLES

Example 1

Construction of an Adapter Plasmid for the Generation of Recombinant Adenoviral Vectors Expressing the ceNOS and VEGF121 or FGF4 cDNAs To construct an adapter plasmid that allows the generation of a recombinant adenoviral vector expressing both the NO synthase cDNA and the cDNA of an angiogenic growth factor, we have used the internal ribosome entry site (IRES) of the encephalomyocarditis virus (ECMV, Jang et al., J. Virol. 62, 2636–2643, 1998). In this example, we have used the cDNA encoding the VEGF121 isoform (Tischer et al., J. Biol. Chem. 266, 11947–11954, 1991) and the FGF4 isoform (Delli-Bovi et al., Cell 50, 729–737, 1987) as the angiogenic factors. The sequence encoding VEGF121 was amplified by PCR using total cDNA from human umbilical vein endothelial cells as a template (total RNA was isolated using Trizol procedure, and first strand cDNA was generated using the Superscript II kit; Gibco BRL). A 464 bp fragment spanning VEGF121 signal peptide and the coding sequence was generated using the following primers: VEGF121-f: 5'-GCC TCA TGA ACT TTC TGC TGT C-3' (SEQ. I.D. NO. 1) and VEGF121-r: 5'-CCC CTC GAG TCT AGA TCA CCG CCT CGG CTT GTC ACA TTT TTC TTG TCT TGC-3' (SEQ. I.D. NO. 2). The PCR fragment was digested with RcaI and XhoI and purified from a 1-% agarose gel using the QIAquick gel extraction kit (Qiagen). To amplify the FGF4 coding sequence, a PCR was carried out using the following primers: FGF4-f: 5'-GGC ACA TGT CGG GGC CCG GGA C-b 3' (SEQ. I.D. NO. 3) and FGF4-r: 5'-CCC CTC GAG TCT AGA TCA CAG CCT GGG GAG GAA GTG G-3' (SEQ. I.D. NO. 4). The resulting 641 bp fragment was digested with AflIII and XhoI and purified from a 1-% agarose gel (QIAquick kit). pBr/pTkEMCVNeo/2 (WO96/35798) was digested with NcoI, and the 1726 bp fragment was recovered by electrophoresis and purified (QIAquick kit). this DNA fragment was then digested with XbaI, and the 568 bp fragment, which contains the EMCV IRES sequence, was purified (QIAquick kit) and inserted at the XbaI and NcoI sites of the pLITMUS29 cloning vector (New England Biolabs). The resulting vector was then cut with NcoI and XhoI, and ligated to the digested PCR fragments (RcaI-XhoI VEGF121 fragment or AflIII-XhoI FGF4 fragment). The plasmids obtained, named pLITMUS29/IRES/VEGF121 and pLITMUS29/IRES/FGF4, were then digested with XbaI and the fragments corresponding to the IRES sequence followed by the VEGF121 or FGF4 cDNA were inserted into the pAdApt/ceNOS adapter vector (described below) lineraized with XbaI and dephosphoryled (bacterial alkaline phosphatase, Gibco BRL). The resulting plasmids were checked by sequencing to search for correct adapter plasmids, named pAdApt/ceNOS/VEGF121 and pAdApt/ceNOS/FGF4. They contain the CMV promoter followed by the ceNOS cDNA, the IRES sequence, and the VEGF121 or FGF4 cDNA, respectively. Recombinant adenoviral vectors derived from pAdApt/ceNOS/VEGF121 and pAdApt/ceNOS/FGF4 introduce a bicistronic mRNA in the infected cells that is transcribed from the CMV promoter and facilitates the translation of both NO synthase and the angiogenic factor (VEGF121/FGF4).

Example 2

Generation of Producer Cell Lines for the Production of Recombinant Adenoviral Vectors Deleted in Early Region 1 and Early Region 2A This example describes the generation of cell lines for the production of recombinant adenoviral vectors that are deleted in early region 1 (E1) and early region 2A (E2A). The producer cell lines complement for the E1 and E2A deletion from recombinant adenoviral vectors in trans by constitutive expression of the E1 and E2A genes, respectively. The pre-established Ad5-E1 transformed human embryo retinoblast cell line PER.C6 (WO 97/00326) and Ad5 transformed human embryo kidney cell line 293 (Graham, 1977) were further equipped with E2A expression cassettes. The adenoviral E2A gene encodes a 72 kDa DNA Binding Protein (DBP) which has a high affinity for single stranded DNA. Because of this feature, constitutive expression of DBP is toxic for cells. The ts125E2A mutant encodes a DBP which has a Pro→Ser substitution of amino acid 413 (van der Vliet, 1975). Due to this mutation, the ts125E2A encoded DBP is fully active at the permissive temperature of 32° C., but does not bind to ssDNA at the non-permissive temperature of 39° C. This allows the generation of cell lines that constitutively express E2A which is not functional and is not toxic at the non-permissive temperature of 39° C., but becomes functional after a temperature switch to the permissive temperature of 32° C.

Example 2A

Generation of Plasmids Expressing Wildtype E2A- or Temperature Sensitive ts125E2A pcDNA 3wtE 2A: The complete wildtype early region 2A (E2A) coding region was amplified from the plasmid pBR/

Ad.Bam-rITR (ECACC deposit P97082122) with the primers DBPpcr1 and DBPpcr2 using the Expand™ Long Template PCR system according to the standard protocol of the supplier (Boehringer Mannheim). PCR was performed on a Biometra Trio Thermoblock, amplification program: 94° C. for 2 minutes, 1 cycle; 94° C. for 10 seconds+51° C. for 30 seconds+68° C. for 2 minutes, 1 cycle; 94° C. for 10 seconds+58° C. for 30 seconds+68° C. for 2 minutes, 10 cycles; 94° C. for 10 seconds+582 C. for 30 seconds +68° C. for 2 minutes with 10 seconds extension per cycle, 20 cycles; 68° C. for 5 minutes, 1 cycle. The primer DBPpcr1: CGG GAT CCG CCA CCA TGG CCA GTC GGG AAG AGG AG (5' to 3' ) (SEQ. I.D. NO. 5) contains a unique BamHI restriction site (underlined) 5' of the Kozak sequence (italic) and start codon of the E2A coding sequence. The primer DBPpcr2: CGG AAT TCT TAA AAA TCA AAG GGG TTC TGC CGC (50' to 3') (SEQ. I.D. NO. 6) contains a unique EcoRI restriction site (underlined) 3' of the stop codon of the E2A coding sequence. The bold characters refer to sequences derived from the E2A coding region. The PCR fragment was digested with BamHI/EcoRI and cloned into BamHI/EcoRI digested pcDNA3 (Invitrogen), giving rise to pcDNA3wtE2A.

pcDNA 3tsE 2A: The complete ts125E2A coding region was amplified from DNA isolated from the temperature sensitive adenovirus mutant H5ts125(Ensinger and Ginsberg, 1972;van der Vliet, 1975). The PCR amplification procedure was identical to that for the amplification of wtE2A the PCR fragment was digested with BamHI/EcoRI and cloned into BamHI/EcoRI digested pcDNA3 (Invitrogen), giving rise to pcDNA3tsE2A. The integrity of the coding sequence of wtE2A and tsE2A was confirmed by sequencing.

Example 2B

Growth Characteristics of Producer Cells for the Production of Recombinant Adenoviral Vectors Cultured at 32-,37- and 39° C.

PER.C6 cells were cultured in Dulbecco's Modified Eagle Medium (DMEM, Gibco BRL) supplemented with 10% Foetal Bovine Serum (FBS, Gibco BRL) and 10 mM $MgCl_2$ in a 10% $CO_2$ atmosphere at either 32° C., 37° C. or 39° C. At day 0, a total of $1\times10^6$ PER.C6 cells were seeded per 25 $cm^2$ tissue culture flask (Nunc) and the cells were cultured at either 32° C., 37° C. or 39° C. At day 1–8, cells were counted. FIG. 1 shows that the growth rate and the final cell density of the PER.C6 culture at 39° C. is comparable to that at 37° C. The growth rate and final density of the PER.C6 culture at 32° C. were slightly reduced as compared to that at 37° C. or 39° C. No significant cell death was observed at any of the incubation temperatures. Thus PER.C6 performs very well both at 32° C. and 39° C., the permissive and non-permissive temperature for ts125E2A, respectively.

Example 2C

Transfection of PER.C6 and 293 with E2A Expression Vectors; Colony Formation and Generation of Cell Lines One day prior to transfection, $2\times10^6$ PER.C6 cells were seeded per 6 cm tissue culture dish (Greiner) in DMEM, supplemented with 10% FBS and 10 mM $MgCl_2$ and incubated at 37° C. in a 10% $CO_2$ atmosphere. The next day, the cells were transfected with 3- , 5- or 8 μg of either pcDNA3, pcDNA3wtE2A or pcDNA3tsE2A plasmid DNA per dish, using the LipofectAMINE PLUS™ Reagent Kit according to the standard protocol of the supplier (Gibco BRL), except that the cells were transfected at 39° C. in a 10% $CO_2$ atmosphere. After the transfection, the cells were constantly kept at 39° C., the non-permissive temperature for ts125E2A. Three days later, the cells were put on DMEM, supplemented with 10% FBS, 10 mM $MgCl_2$ and 0.25 mg/ml G418 (Gibco BRL) and the first G418 resistant colonies appeared at 10 days post transfection. As shown in table 1, there was a dramatic difference between the total number of colonies obtained after transfection of pcDNA3 (~200 colonies) or pcDNA3tsE2A (~100 colonies) and pcDNA3wtE2A (only 4 colonies). These results indicate that the toxicity of constitutively expressed E2A can be overcome by using a temperature sensitive mutant of E2A (ts125E2A) and culturing of the cells at the non-permissive temperature of 39° C.

From each transfection, a number of colonies was picked by scraping the cells from the dish with a pipette. The detached cells were subsequently put into 24 wells tissue culture dishes (Greiner) and cultured further at 39° C. in a 10% $CO_2$ atmosphere in DMEM, supplemented with 10% FBS, 10 mM $MgCl_2$ and 0.25 mg/ml G418. As shown in table 1, 100% of the pcDNA3 transfected colonies (4/4) and 82% of the pcDNA3tsE2A transfected colonies (37/45) were established to stable cell lines (the remaining 8 pcDNA3tsE2A transfected colonies grew slowly and were discarded). In contrast, only 1 pcDNA3wtE2A transfected colony could be established. The other 3 died directly after picking.

Figure 2:
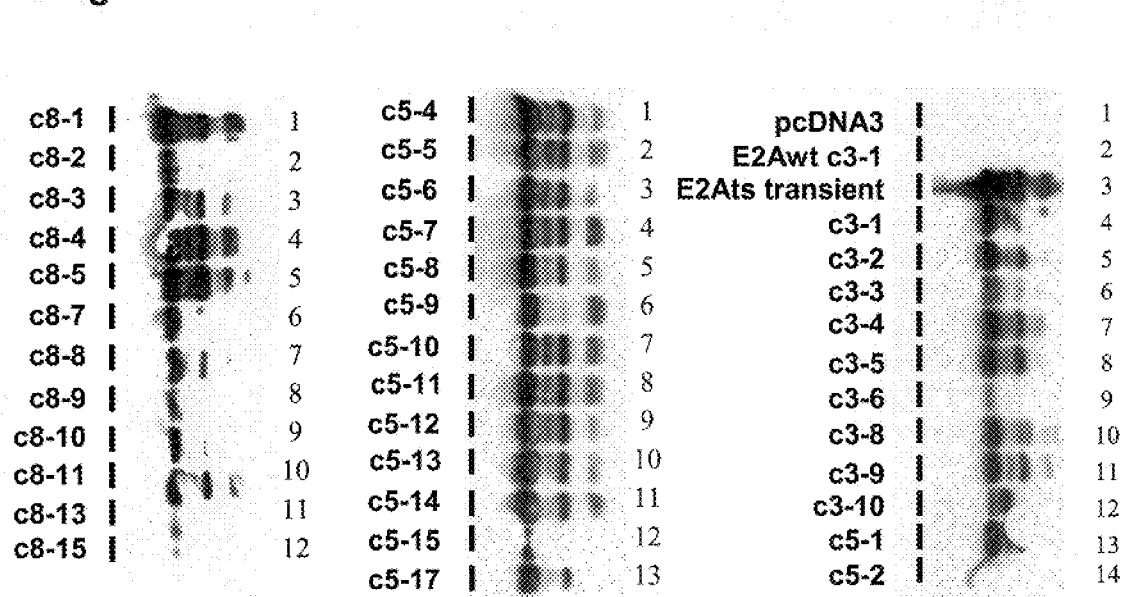
FIG. 2. Western blot of different PER.C6 clones transfected with E2Ats125.

Next, the E2A expression levels in the different cell lines were determined by Western blotting. The cell lines were seeded on 6 well tissue culture dishes and sub-confluent cultures were washed twice with PBS (NPBI) and lysed and scraped in RIPA (1% NP-40, 0.5% sodium deoxycholate and 0.1% SDS in PBS, supplemented with 1 mM phenylmethylsulfonylfluoride and 0.1 mg/ml trypsin inhibitor). After 15 minutes incubation on ice, the lysates were cleared by centrifugation. Protein concentrations were determined by the Bio-Rad protein assay, according to standard procedures of the supplier (BioRad). Equal amounts of whole-cell extract were fractionated by SDS-PAGE on 10% gels. Proteins were transferred onto Immobilon-P membranes (Millipore) and incubated with the αDPB monoclonal antibody B6 (Reich, 1983). The secondary antibody was a horseradish-peroxidase conjugated goat anti mouse antibody (BioRad). The Western blotting procedure and antibody incubations were performed according to the protocol provided by Millipore. The antibody complexes were visualised with the ECL detection system according to the manufactuer's protocol (Amersham). FIG. 2 shows that all of the cell lines derived from the pcDNA3tsE2A transfection express the 72-kDa E2A protein (upper panel, lanes 4–14; middle panel, lanes 1–13; lower panel, lanes 1–12). In contrast, the only cell lines derived from the pcDNAwtE2A transfection did not express the E2A protein (lane 2). No E2A protein was detected in extract from a cell line derived from the pcDNA3 transfection (lane 1), which serves as a negative control. Extract from PER.C6 cells transiently transfected with pcDNA3ts125 (lane 3) served as a positive control for the Western blot procedure. These data confirm that constitutive expression of wtE2A is toxic for cells and that this toxicity can be circumvented by using the ts125 mutant of E2A.

In contrast to PER.C6 cells, the culturing of 293 cells at 39° C. is troublesome. Therefore, the transfection of 293 cells with either pcDNA3, pcDNA3wtE2A or pcDNA3tsE2A was performed at 37° C. in an atmosphere of 10% $CO_2$, a semi-permissive temperature for ts125E2A encoded DBP. A day prior to transfection, 293 cells were seeded in, supplemented with 10% FBS and 10 mM $MgCl_2$, at a density of $3.6 \times 10^5$ cells per 6 cm tissue culture dish (Greiner). Five hours before transfection, cells received fresh medium. Cells were transfected with 7.2 µg of either pcDNA3, pcDNA3wtE2A or pcDNA3tsE2A plasmid DNA using the Calcium Phosphate Transfection System according to the standard protocol of the supplier (Gibco BRL). Two days post transfection, cells were put on selection medium, i.e. DMEM supplemented with 10% FBS, 10 mM, $MgCl_2$ and 0.1 mg/ml G418. The first colonies appeared at days 12 post transfection. The total number of colonies obtained after transfection of pcDNA3 (~100 colonies) or pcDNA3tsE2A (~25 colonies) was significantly higher than that obtained after transfection of pcDNA3wtE2A (only 2 colonies). These results again show that constitutively expressed E2A is toxic for cells and that this toxicity can be circumvented by using ts125E2A. Moreover, it shows that this is not specific for PER.C6 cells, but that it applies to eukaryotic cells in general (e.g. 293 cells).

Example 2D

Complementation of the E2A Deletion in Ad5. dl802 by PER.C6 Cells Constitutively Expressing ts125E2A The adenovirus Ad5.dl802 is an Ad 5 derived vector deleted for the major part of the E2A coding region and does not produce functional DBP (Rice 1985). Ad5.dl802 was used to test the E2A trans-complementing activity of PER.C6 cells constitutively expressing ts125E2A. Parental PER.C6 cells or PER.C6tsE2A clone 3–9 were cultured in DMEM, supplemented with 10% FBS and 10 mM $MgCl_2$ at 39° C. and 10% $CO_2$ in 25 cm² flasks and either mock infected or infected with Ad5.dl802 at an m.o.i. of 5. Subsequently the infected cells were cultured at 32° C. and cells were screened for the appearance of a cytopathic effect (CPE) as determined by changes in cell morphology and detachment of the cells from the flask. Table 2 shows that full CPE appeared in the Ad5.dl802 infected PER.C6tsE2A clone 3–9 within 2 days. No CPE appeared in the Ad5.dl802 infected PER.C6 cells or the mock infected cells. These data show that PER.C6 cells constitutively expressing ts125E2A complement in trans for the E2deletion in the Ad5. dl802 vector at the permissive temperature of 32° C.

Example 3

Serum Free Suspension Culture of PER.C6TSE2A Cell Lines

Figure 3:
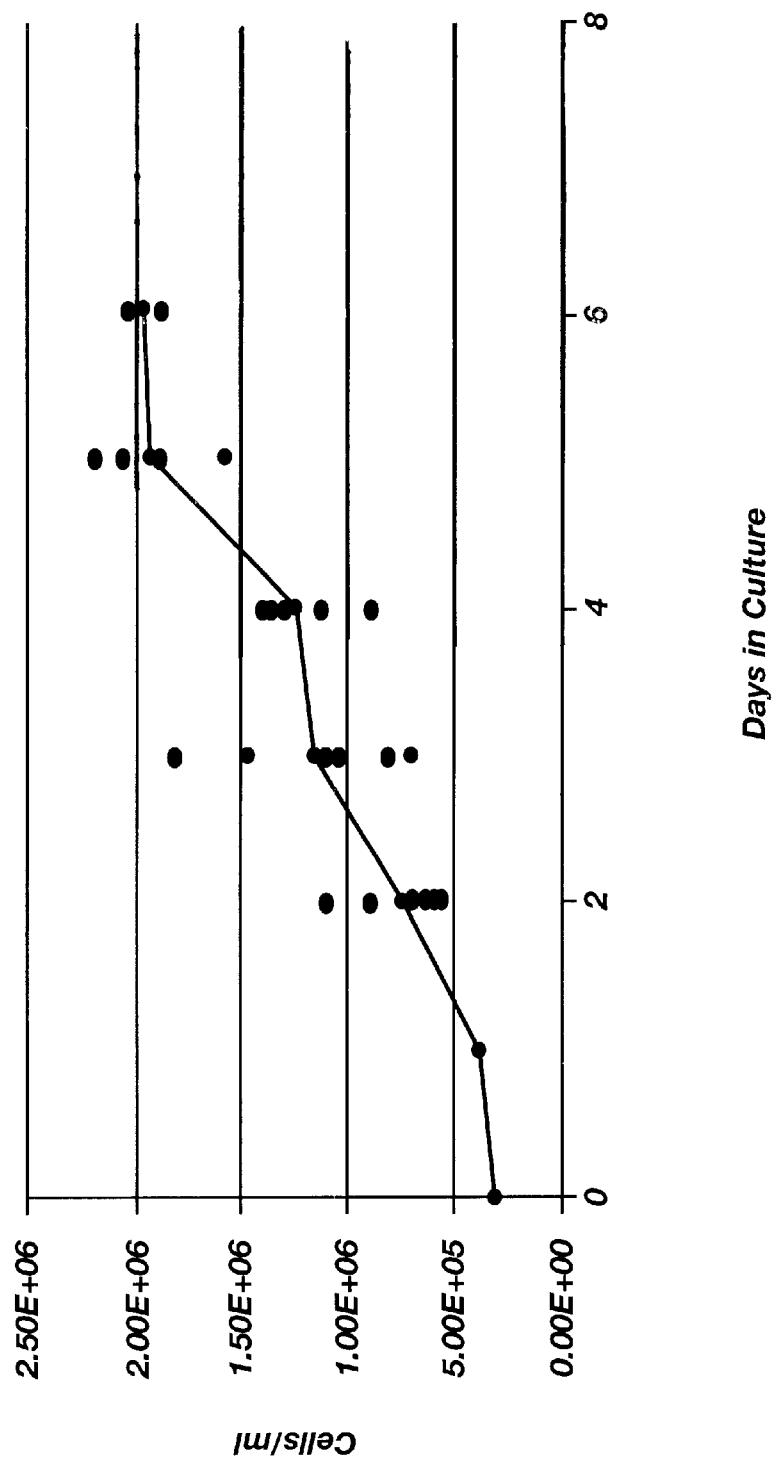
FIG. 3. Suspension growth characteristics of PER.C6ts125E2A C5–9 cells.

Large scale production of recombinant adenoviral vectors for human gene therapy requires an easy and upscalable culturing method for the producer cell line, preferably a suspension culture, in medium devoid of any human or animal constituents. To that end, the cell line PER.C6tsE2A c5–9 (designated c5–9) was cultured at 39° C. and 10% $CO_2$ in a 175 cm² tissue culture flask (Nunc) in DMEM, supplemented with 10% FBS and 10 mM $MgCl_2$. A sub-confluency (70–80% confluent), the cells were washed with PBS (NPBI) and the medium was replaced by 25 ml serum free suspension medium Ex-cell™ 525 (JRH) supplemented with 1×L-Glutamin (Gibco BRL), hereafter designated SFM. Two days later, cells were detached from the flask by flicking and the cells were centrifuged at 1000 rpm for 5 minutes. The cell pellet was resuspended in 5 ml SFM and 0.5 ml cell suspension was transferred to a 80 cm² tissue culture flask (Nunc), together with 12 ml fresh SFM. After 2 days, cells were harvested (all cells are in suspension) and counted in a Burker cell counter. Next, the cells were seeded in a 125 ml tissue culture erlenmeyer (Corning) at a seeding density of $3 \times 10^5$ cells per ml in a total volume of 20 ml SFM. Cells were further cultured at 125 RPM on an orbital shaker (GFL) at 39° C. in a 10% $CO_2$ atmosphere. Cells were counted at day 1–6 in a Burker cell counter. In FIG. 3, the mean growth curve from 8 cultures is shown. PER.C6tsE2A c5–9 performs well in serum free suspension culture. The maximum cell density of approximately $2 \times 10^6$ cells per ml is reached within 5 days of culture.

Example 4

Plasmid Based System for the Generation of Recombinant Adenoviral Vectors Deleted in Early Region 1 and Early Region 2

Example 4A

Generation of pBr/Ad.Bam-rITR (ECACC Deposit P9708212)

In order to facilitate blunt end cloning of the ITR sequences, wild-type human adenovirus type 5 (Ad5) DNA was treated with Klenow enzyme in the presence of excess dNTPs. After inactivation of the Klenow enzyme and purification by phenol/chloroform extraction followed by ethanol precipitation, the DNA was digested with BamHI. This DNA preparation was used without further purification in a ligation reaction with pBr322 derived vector DNA prepared as follows: pBr322 DNA was digested with EcoRV and BamHI, dephosphorylated by treatment with TSAP enzyme (Life Technologies) and purified on LMP agarose enzyme (SeaPlaque GTG). After transformation into competent E. Coli DH5a (Life Techn.) and analysis of ampiciline resistant colonies, one clone was selected that showed a digestion pattern as expected for an insert extending from the BamHI site in Ad5 to the right ITR.

Sequence analysis of the cloning border at the right ITR revealed that the most 3' G residue of the ITR was missing, the remainder of the ITR was found to be correct. Said missing G residue is complemented by the other ITR during replication.

Example 4B

Generation of pBr/Ad.Sal-rITR (ECACC Deposit P97082119)

pBr/Ad.Bam-rITR was digested with BamHI and SalI. The vector fragment including the adenovirus was isolated in LMP agarose (SeaPlaque GTG) and ligated to a 4.8 kb SalI-BamHI fragment obtained from wt Ad5 DNA and purified with the Geneclean II kit (Bio 101, Inc.). One clone was chosen and the integrity of the Ad5 sequences was determined by restriction enzyme analysis. Clone pBR/Ad.Sal-rITR contains adeno type 5 sequences from the SalI site at bp 16746 up to and including the rITR (missing the most 3' G residue).

Example 4C

Generation of pBr/Ad.AflII-Bam (ECACC deposit P97082114)

First pBr/Ad.Cla-Bam (ECACC deposit P97082117) was generated. Wt Adeno type 5 DNA was digested with ClaI and BamHI, and the 20.6 kb fragment was isolated from gel by electroelution. pBr322 was digested with the same enzymes and purified from agarose gel by Geneclean. Both fragments were ligated and transformed into competent DH5α. The resulting clone pBr/Ad.Cla-Bam was analysed by restriction enzyme digestion and shown to contain an insert with adenovirus sequences from bp 919 to 21566. Next pBr/Ad.Cla-Bam was linearised with EcoRI (in pBr/322) and partially digested with AflII. After heat inactivation of AflII for 20' at 65° C. the fragment ends were filled in with Klenow enzyme. The DNA was then ligated to a blunt double stranded oligo linker containing a PacI site (5'-AATTGTCTTAATTAACCGCTTAA-30') SEQ. I.D. NO. 7). This linker was made by annealing the following two oligonucleotides: 5'-AATTGTCTTAATTAACCGC-3' (SEQ. I.D. NO. 8) and 5'-AATTGCGGTTAATTAAGAC-3' (SEQ. I.D. No. 9), followed by blunting with Klenow enzyme. After precipitation of the ligated DNA to change buffer, the ligations were digested with an excess PacI enzyme to remove concatameres of the oligo. The 22016 bp partial fragment containing Ad5 sequences from bp 3534 up to 21566 and the vector sequences, was isolated in LMP agarose (SeaPlaque GTG), religated and transformed into competent DH5α. One clone that was found to contain the PacI site and that had retained the large adeno fragment was selected and sequenced at the 5' end to verify correct insertion of the PacI linker in the (lost) AflII site.

Example 4D

Generation of pBr/Ad.Bam-rITRpac#2 (ECACC Deposit P97082120) and pBr/Ad.Bam-rITR#8 (ECACC Deposit P97082121)

To allow insertion of a PacI site near the ITR of Ad5 in clone pBr/Ad.Bam-rITR about 190 nucleotides were removed between the ClaI site in the pBr322 backbone and the start of the ITR sequences. This was done as follows: pBr/Ad.Bam-rITR was digested with ClaI and treated with nuclease Bal31 for varying lengths of time (2', 5', 10' and 15'). The extend of nucleotide removal was followed by separate reactions on pBr322 DNA (also digested at the ClaI site), using identical buffers and conditions. Bal31 enzyme was inactivated by incubation at 75° C. for 10', the DNA was precipitated and resuspended in a smaller volume TE buffer. To ensure blunt ends, DNAs were further treated with T4 DNA polymerase in the presence of excess dNTPs. After digestion of the (control) pBr322 DNA with SalI, satisfactory degradation ("150 bp) was observed in the samples treated for 10' or 15'. The 10' or 15' treated pBr/Ad.Bam-rITR samples were then ligated to the above described blunted PacI linkers (See pBr/Ad.AflII-Bam). Ligations were purified by precipitation, digested with excess PacI and separated from the linkers on an LMP agarose gel. After religation, DNAs were transformed into competent DH5α and colonies analysed. Ten clones were selected that showed a deletion of approximately the desired length and these were further analysed by T-track sequencing (T7 sequencing kit, Pharmacia Biotech). Two clones were found with the PacI linker inserted just downstream of the rITR. After digestion with PacI, clone #2 has 28 bp and clone #8 has 27 bp attached to the ITR.

Example 4E

Generation of pWE/Ad.AflII-rITR (ECACC Deposit P97082116)

Cosmid vector pWE15 (Clontech) was used to clone larger Ad5 inserts. First, a linker containing a unique PacI site was inserted in the EcoRI sites of pWE15 creating pWE.pac. To this end, the double stranded PacI oligo as described for pBr/Ad.AflII-BamHI was used but now with its EcoRI protruding ends. The following fragments were then isolated by electro-elution from agarose gel: pWE.pac digested with PacI, pBr/AflII-Bam digested with PacI and BamHI and pBr/Ad.Bam-rITR#2 digested with BamHI and PacI. These fragments were ligated together and packaged using λ phage packaging extracts (Stratagene) according to the manufacturer's protocol. After infection into host bacteria, colonies were grown on plates and analysed for presence of the complete insert. pWE/Ad.AflII-rITR contains all adenovirus type 5 sequences from bp 3534 (AflII site) up to and including the right ITR (missing the most 3' G residue).

Example 4F

Generation of pWE/Ad.AflII-EcoRI pWE.pac was digested with ClaI and 5' protruding ends were filled using Klenow enzyme. The DNA was then digested with PacI and isolated from agarose gel. pWE/AflII-rITR was digested with EcoRI and after treatment with Klenow enzyme digested with PacI. The large 24 kb fragment containing the adenoviral sequences was isolated from agarose gel and ligated to the ClaI-digested and blunted pWE.pac vector using the Ligation Express™ kit from Clontech. After transformation of Ultracompetent XL10-Gold cells from Stratagene, clones were identified that contained the expected insert. pWE/AflII-EcoRI contains Ad5 sequences from bp 3534–27336.

Example 4G

Generation of pWE/Ad.AflII-rITRΔE2A

Deletion of the E2A coding sequences from pWE/Ad.AflII-rITR (ECACC deposit P97082116) has been accomplished as follows. The adenoviral sequences flanking the E2A coding region at the left and the right site were amplified from the plasmid pBR/Ad.Sal.rITR (ECACC deposit P97082119) in a PCR reaction with the Expand PCR system (Boehringer) according to the manufacturers protocol. The following primers were used:
Right flanking sequences (corresponding Ad5 nucleotides 24033 to 25180):

ΔE2A.SnaBI: 5'-GGC GTA CGT AGC CCT GTC GAA AG-3' (SEQ. I.D. No. 10)

ΔE2A.DBP-start: 5'-CCA <u>ATG CAT</u> TCG AAG TAC TTC CTT CTC CTA TAG GC-3' (SEQ. I.D. No. 11)

The amplified DNA fragment was digested with SnaBI and NsiI (NsiI site is generated in the primer ΔE2A.DBP-start, underlined).
Left flanking sequences (corresponding Ad5 nucleotides 21557 to 22442):

ΔE2A.DBP-stop: 5'-CCA <u>ATG CAT</u> ACG GCG CAG ACG G-3' (SEQ. I.D. NO. 12)

ΔE2A.BamHI: 5'-GAG GTG GAT CCC ATG GAC GAG-3' (SEQ. I.D. NO. 13)

The amplified DNA was digested with BamHI and NsiI (NsiI site is generated in the primer ΔE2A.DBP-stop, underlined). Subsequently, the digested DNA fragments were ligated into SnaBI/BamHI digested pBr/Ad.Sal-rITR. Sequencing confirmed the exact replacement of the DBP coding region with a unique NsiI site in plasmid pBr/Ad.Sal-rITRΔE2A. The unique NsiI site can be used to introduce an expression cassette for a gene to be transduced by the recombinant vector. Next, the plasmid pWE/Ad.AflII-rITRΔE2A was generated. The plasmid pBr/Ad.Sal-rITRΔE2A was digested with BamHI and SpeI. The 3.9 Kb fragment in which the E2A coding region was replaced by the unique NsiI site was isolated. The pWE/Ad.AflII-rITR was digested with BamHI and SpeI. The 35 Kb DNA fragment, from which the BamHI/SpeI fragment containing the E2A coding sequence was removed, was isolated. The fragments were ligated and packaged using λ phage packaging extracts according to the manufacturers protocol (Stratagene), yielding the plasmid pWE/Ad.AflII-rITRΔE2A.\

Example 4H

Generation of the Adapter Plasmids

Adapter plasmid pMLPTK (patent application EP 95202213) was modified as follows: SV40 polyA sequences were amplified with primer SV40-1 (introduces a BamHI site) and SV40-2 (introduces a BglII site). In addition, Ad5 sequences present in this construct (from nt. 2496 to nt. 2779; Ad5 sequences nt. 3511 to 3794) were amplified with primers Ad5-1 (introduces a BglII site) and Ad5-2.

SV40-1: 5'-GGG GGATCCGAACTTGTTTATTGCAGC-3' (SEQ. I.D. NO. 14)

SV40-2: 5'-GGGAGATCTAGACATGATAAGATAC-3' (SEQ. I.D. NO. 15)

Ad5-1: 5'-GGG AGATCTGTACTGAAATGTGTGGGC-3' (SEQ. I.D. NO. 16)

Ad5-2: 5'-GGAGGCTGCAGTCTCCAACGGCGT-3' (SEQ. I.D. NO. 17)

Both PCR fragments were digested with BglII and ligated. The ligation product was amplified with primers SV40-1 and Ad5-2 and digested with BamHI and AflII. The digested fragment was then ligated into pMLP.TK predigested with the same enzymes. The resulting construct, named pMLPI.TK (described in WO 97/00326), contains a deletion in adenovirus E1 sequences from nt. 459 to nt. 3510.

This plasmid was used as the starting material to make a new vector in which nucleic acid molecules comprising specific promoter and gene sequences can be easily exchanged. First, a PCR fragment was generated from pZipΔMo+PyF101 (N⁻) template DNA (described in PCT/NL96/00195) with the following primers: LTR-1: 5'-CTG TAC GTA CCA GTG CAC TGG CCT AGG CAT GGA AAA ATA CAT AAC TG-3' (SEQ. I.D. NO. 18) and LTR-2: 5'-GCG GAT CCT TCG AAC CAT GGT AAG CTT GGT ACC GCT AGC GTT AAC CGG GCG ACT CAG TCA ATC G-3' (SEQ. I.D. NO. 19). Pwo DNA polymerase (Boehringer Mannheim) was used according to manufacturers protocol with the following temperature cycles: once 5' at 95° C.; 3' at 55° C.; and 1' at 72° C., and 30 cycles of 1' at 95° C., 1' at 60° C., 1' at 72° C., followed by once 10' at 72° C. The PCR product was then digested with BamHI and ligated into pMLP10 (Levrero et al., 1991; Gene 101, 195–202) digested with PvuII and BamHI, thereby generating vector pLTR10. This vector contains adenoviral sequences from bp 1 up to bp 454 followed by a promoter consisting of a part of the Mo-MuLV LTR having its wild-type enhancer sequences replaced by the enhancer from a mutant polyoma virus (PyF101). The promoter fragment was designated L420. Sequencing confirmed correct amplification of the LTR fragment however the most 5' bases in the PCR fragment were missing so that the PvuII site was not restored. Next, the coding region of the murine HSA gene was inserted. pLTR10 was digested with BstBI followed by Klenow treatment and digestion with NcoI. The HSA gene was obtained by PCR amplification on pUC18-HSA (Kay et al., 1990; J. Immunol. 145, 1952–1959) using the following primers: HSA1, 5'-GCG CCA CCA TGG GCA GAG CGA TGG TGG C-3' (SEQ. I.D. NO. 20) and HSA2, 5'-GTT AGA TCT AAG CTT GTC GAC ATC GAT CTA CTA ACA GTA GAG ATG TAG AA-3' (SEQ. I.D. NO. 21). The 269 bp amplified fragment was subcloned in a shuttle vector using the NcoI and BglII sites. Sequencing confirmed incorporation of the correct coding sequence of the HSA gene, but with an extra TAG insertion directly following the TAG stop codon. The coding region of the HSA gene, including the TAG duplication was then excised as a NcoI (sticky)-SalI (blunt) fragment and cloned into the 3.5 kb NcoI (sticky)/BstBI (blunt) fragment from pLTR10, resulting in pLTR-HSA10.

Finally, pLTR-HSA10 was digested with EcoRI and BamHI after which the fragment containing the left ITR, packaging signal, L420 promoter and HSA gene was inserted into vector pMLPI.TK digested with the same enzymes and thereby replacing the promoter and gene sequences. This resulted in the new adapter plasmid pAd5/L420-HSA that contains convenient recognition sites for various restriction enzymes around the promoter and gene sequences. SnaBI and AvrII can be combined with HpaI, NheI, KpnI, HindIII to exchange promoter sequences, while the latter sites can be combined with the ClaI or BamHI sites 3' from HSA coding region to replace genes in this construct.

Another adapter plasmid that was designed to allow easy exchange of nucleic acid molecules was made by replacing the promoter, gene and poly A sequences in pAd5/L420-HSA with the CMV promoter, a multiple cloning site, an intron and a poly-A signal. For this purpose, pAd/L420-HSA was digested with AvrII and BglII followed by treatment with Klenow to obtain blunt ends. The 5.1 kb fragment with pBr322 vector and adenoviral sequences was isolated and ligated to a blunt 1570 bp fragment from pcDNA1/amp (Invitrogen) obtained by digestion with HhaI and AvrII followed by treatment with T4 DNA polymerase. This adapter plasmid was named pAd5/Clip. To enable removal of vector sequences from the adenoviral fragment pAd5/Clip was partially digested with EcoRI and the linear fragment was isolated. An oligo of the sequence 5' TTAAGTCGAC-3' was annealed to itself resulting in a linker with a SalI site and EcoRI overhang. The linker was ligated to the partially digested pAd5/Clip vector and clones were selected that had the linker inserted in the EcoRI site 23 bp upstream of the left adenovirus ITR in pAd5/Clip resulting in pAd5/Clipsal.

Generation of adapter plasmids pAdMire and pAdApt

To create an adapter plasmid that only contains a polylinker sequence and no promoter or polyA sequences, pAd5/L420-HSApac was digested with AvrII and BglII. The vector fragment was ligated to a linker oligonucleotide digested with the same restriction enzymes. The linker was made by annealing oligos of the following sequence:

PLL-1: 5'-GCC ATC CCT AGG AAG CTT GGT ACC GGT GAA TTC GCT AGC GTT AAC GGA TCC TCT AGA CGA GAT CTG G-3' (SEQ. I.D. NO. 22) and PLL-2: 5'-CCA GAT CTC GTC TAG AGG ATC CGT TAA CGC TAG CGA ATT CAC CGG TAC CAA GCT TCC TAG GGA TGG C-3' (SEQ. I.D. NO. 23)

The annealed linkers were digested with AvrII and BglII and separated from small ends by column purification (Qiaquick nucleotide removal kit) according to manufacturers recommendations. The linker was then ligated to the AvrII/BglII digested pAd5/L420-HSApac fragment. A clone, named pAdMire, was selected that had the linker incorporated and was sequenced to check the integrity of the insert. Adapter plasmid pAdMire enables easy insertion of complete expression cassettes.

An adapter plasmid containing the human CMV promoter that mediates high expression levels in human cells was constructed as follows: pAd5/L420-HSApac was digested with AvrII and 5' protruding ends were filled in using Klenow enzyme. A second digestion with HindIII resulted in removal of the L420 promoter sequences. The vector fragment was isolated and ligated to a PCR fragment containing the CMV promoter sequence. This PCR fragment was obtained after amplification of CMV sequences from pCM-VLacI (Stratagene) with the following primers:

CMVplus: 5'-GATCGGTACCACTGCAGTGGTCAATATTGGCCATTAGCC-3' (SEQ. I.D. NO. 24) and

CMVminA: 5'-GATCAAGCTTCCAATGCACCGTTCCCGGC-3' (SEQ. I.D. NO. 25).

The PCR fragment was first digested with PstI (underlined in CMVplus) after which the 3'-protruding ends were removed by treatment with T4 DNA polymerase. Then the DNA was digested with HindIII (underlined in CMVminA) and ligated into the above described pAd5/L420-HSApac vector fragment digested with AvrII and HindIII. The resulting plasmid was named pAd5/CMV-HSApac. This plasmid was then digested with HindIII and BamHI and the vector fragment was isolated and ligated to the polylinker sequence obtained after digestion of pAdMire with HindIII and BglII. The resulting plasmid was named pAdApt (FIG. 3). Adapter plasmid pAdApt contains nucleotides −735 to +95 of the human CMV promoter (Boshart et al., 1985; A very strong enhancer is located upstream of an immediate early gene of human cytomegalovirus. Cell 41,521–530, 1985).

Generation of pAdApt-ceNOS

Figure 4:
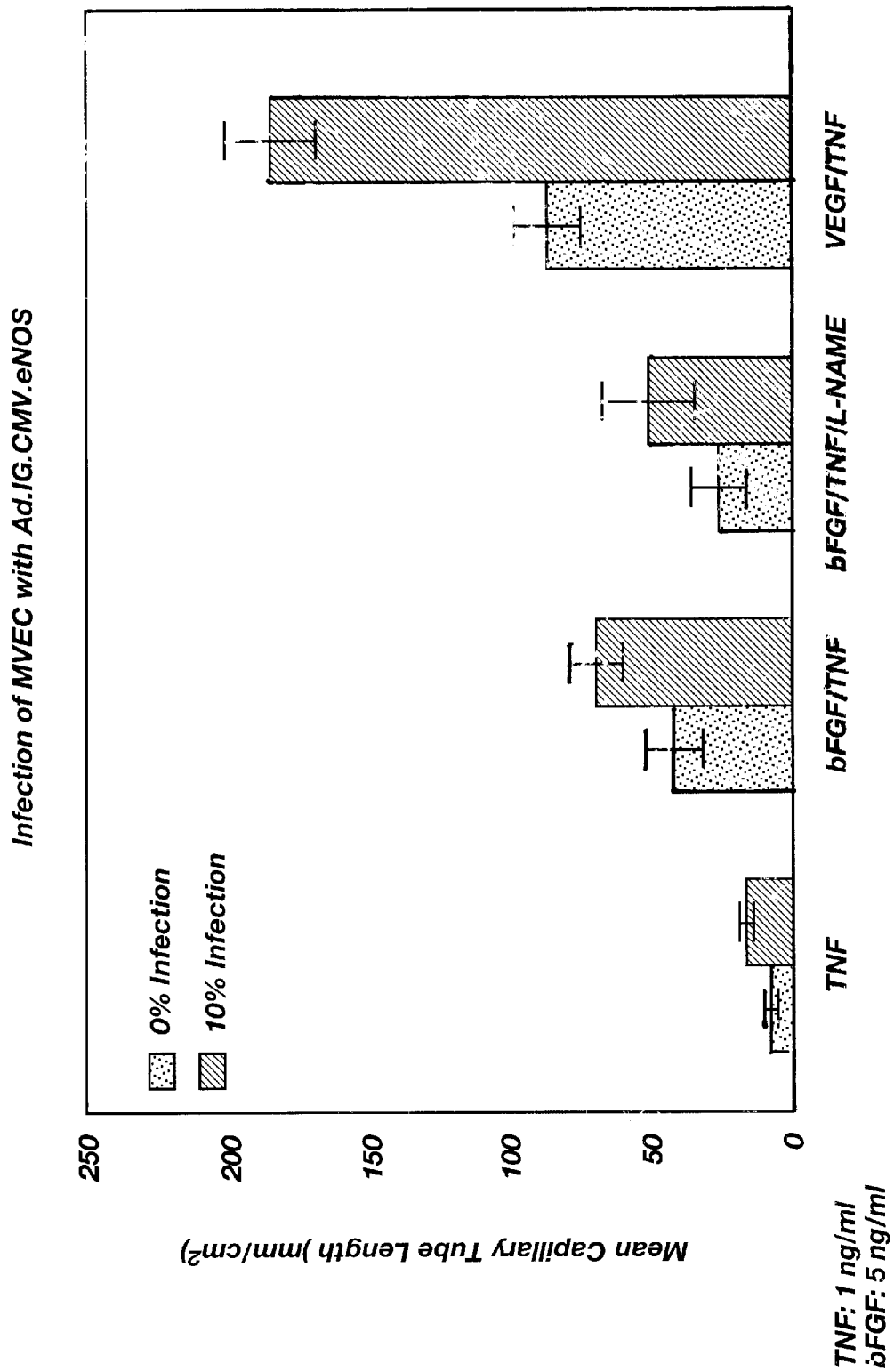
FIG. 4. Mean capillary tube length of tubular structures in cultured MVEC cells infected with Ad.IG.CMV.eNOS in the presence or absence of TNF, bFGF, L-NAME and or VGEF as indicated.

Plasmid pAC(d)CMVceNOS (described in Janssens et al. 1998; Human endothelial nitric oxide synthase gene transfer inhibits vascular smooth muscle cell proliferation and neointima formation after balloon injury in rats. Circulation 97, 1274–1281) was digested with EcoRI and the ends were filled in using Klenow enzyme. The ceNOS insert was then removed by digestion with XbaI and isolated from gel using the GeneClean kit II (Bio 101 Inc.). pAd/Clip was digested with BamHI and the ends were also filled in using Klenow followed by digestion with XbaI and isolation from gel. Ligation of the two fragments resulted in pAd/Clip-ceNOS. The ceNOS sequence was removed from pAd5/Clip-ceNOS by digestion with HindIII and XbaI and the 3.7 kb ceNOS fragment was isolated from gel using the GeneClean spinkit (Bio101 Inc.) according to the manufacturers instructions. Adapter plasmid pAdApt was also digested with HindIII and XbaI and the linear fragment was isolated as described above. Both fragments were ligated resulting in pAdApt-ceNOS (FIG. 4).

The recombinant adenoviruses IGAdApt and IGAdApt-ceNOS were generated using the above described adapter plasmids and the adenovirus cosmid clone pWE/Ad.AflII-rITR.

Example 5

Generation of Recombinant Adenoviruses

Example 5A

E1-Deleted Recombinant Adenoviruses with wt E3 Sequences

To generate E1 deleted recombinant adenoviruses with the plasmid-based system, the following constructs are prepared: An adapter construct containing the expression cassette with the gene of interest linearised with a restriction enzyme that cuts at the 3' side of the overlapping adenoviral genome fragment, preferably not containing any pBr322 vector sequences, and A complementing adenoviral genome construct pWE/Ad.AflII-rITR digested with PacI. These two DNA molecules are further purified by phenol/chloroform extraction and EtOH precipitation. Co-transfection of these plasmids into an adenovirus packaging cell line, preferably a cell line according to the invention, generates recombinant replication deficient adenoviruses by a one-step homologous recombination between the adapter and the complementing construct.

A general protocol as outlined below and meant as a non-limiting example of the present invention has been performed to produce several recombinant adenoviruses using various adapter plasmids and the Ad.AflII-rITR fragment. Adenovirus packaging cells (PER.C6) were seeded in −25 cm$^2$ flasks and the next day when they were at −80% confluency, transfected with a mixture of DNA and lipofectamine agent (Life Techn.) as described by the manufacturer. Routinely, 40 µl lipofectamine, 4 µgr adapter plasmid and 4 µgr of the complementing adenovirus genome fragment AflII-rITR (or 2 µgr of all three plasmids for the double homologous recombination) are used. Under these conditions transient transfection efficiencies of −50% (48 hrs post transfection) are obtained as determined with control transfections using a pAd/CMV-LacZ adapter. Two days later, cells are passaged to −80 cm$^2$ flasks and further cultured. Approximately five (for the single homologous recombination) to eleven days (for the double homologous recombination) later a cytopathic effect (CPE) is seen, indicating that functional adenovirus has formed. Cells and medium are harvested upon full CPE and recombinant virus is released by freeze-thawing. An extra amplification step in a 80 cm$^2$ flask is routinely performed to increase the yield since at the initial stage the titers are found to be variable despite the occurrence of full CPE. After amplification, viruses are harvested and plaque purified on PER.C6 cells. Individual plaques are tested for viruses with active transgenes.

Until now, four different recombinant adenoviruses, comprising the human interleukin-3 gene, the human endothelial nitric oxide gene, the Tc1A transposase gene, or the bacterial LacZ gene, have been produced using this protocol. In all cases, functional adenovirus was formed and all isolated plaques contained viruses with an active transgene.

Example 5B

E1-Deleted Recombinant Adenoviruses with Modifications in the E2A, E3 and/or E4 Regions Besides replacements in the E1 region, it is possible to delete or replace the E2A region in the adenovirus. This creates the opportunity to use a larger insert or to insert more than one gene without exceeding the maximum packagable size (approximately 105% of wt genome length). Recombinant viruses that are both E1 and E2A deleted are generated by a homologous recombination procedure as described above for E1-replacement vectors using a plasmid-based system consisting of:

an adapter plasmid for E1 replacement according to the invention, with or without insertion of a first gene of interest, the pWE/Ad.AflII-rITRΔE2A fragment, with or without insertion of a second gene of interest.

Generation and propagation of such a virus, requires a complementing cell line for complementation of both E1 and E2A proteins in trans, as described above.

In addition to replacements in the E1 and E2A region, it is also possible to delete or replace (part of) the E3 region in the E1-deleted adenoviral vector, because E3 functions are not necessary for the replication, packaging and infection of the (recombinant) virus. This creates the opportunity to use larger inserts or to insert more than one gene without exceeding the maximum packagable size (approximately 105% of wt genome length). This can be done, e.g., by deleting part of the E3 region in the pBr/Ad.Bam-rITR clone by digestion with XbaI and religation. This removes Ad5 wt sequences 28592–30470 including all known E3 coding regions. Another example is the precise replacement of the coding region of gp19K in the E3 region with a polylinker allowing insertion of new sequences. This, 1) leaves all other coding regions intact and 2) obviates the need for a heterologous promoter since the transgene is driven by the E3 promoter and pA sequences, leaving more space for coding sequences. To this end, the 2.7 kb EcoRI fragment from wt Ad5 containing the 5' part of the E3 region was cloned into the EcoRI site of pBluescript (KS") (Stratagene). Next, the HindIII site in the polylinker was removed by digestion with EcoRV and HincII and subsequent religation. The resulting clone pBS.Eco-Eco/ad5ΔHIII was used to delete the gp19K coding region. Primers 1 (5'-GGG TAT TAG GCC AA AGG CGC A-3') (SEQ. I.D. NO. 26) and 2 (5'-GAT CCC ATG GAA GCT TGG GTG GCG ACC CCA GCG-3') (SEQ. I.D. NO. 27) were used to amplify a sequence from pBS.Eco-Eco/ad5ΔHIII corresponding to sequences 28511 to 28734 in wt Ad5 DNA. Primers 3 (5'-GAT CCC ATG GGG ATC CTT TAC TAA GTT ACA AAG CTA-3') (SEQ. I.D. NO. 28) and 4 (5'-GTC GCT GTA GTT GGA CTG G-3') (SEQ. I.D. NO. 29) were used on the same DNA to amplify Ad5 sequences from 29217 to 29476. The two resulting PCR fragments were ligated together by virtue of the new introduced NcoI site and subsequently digested with XbaI and MunI. This fragment was then ligated into the pBS.Eco-Eco/ad5ΔHIII vector that was digested with XbaI (partially) and MunI generating pBS.Eco-Eco/ad5ΔHIII.Δgp19K. To allow insertion of foreign genes into the HindIII and BamHI site, an XbaI deletion was made in pBS.Eco-Eco/ad5ΔHIII.Δgp19K to remove the BamHI site in the Bluescript polylinker. The resulting plasmid pBS.Eco-Eco/ad5ΔHIIIΔgp19KΔXbaI, contains unique HindIII and BamHI sites corresponding to sequences 28733 (HindIII) and 29218 (BamHI) in Ad5. After introduction of a foreign gene into these sites, either the deleted XbaI fragment is re-introduced, or the insert is recloned into pBS.Eco-Eco/ad5ΔHIII.Δgp19K using HindIII and for example MunI. Using this procedure, we have generated plasmids expressing HSV-TK, hIL-1α, rat IL-3, luciferase or LacZ. The unique SrfI and NotI sites in the pBS.Eco-Eco/ad5ΔHIII.Dgp19K plasmid (with or without inserted gene of interest) are used to transfer the region comprising the gene of interest into the corresponding region of pBr/Ad.Bam-rITR, yielding construct pBr/Ad.Bam-rITRDgp19K (with or without inserted gene of interest). This construct is used as described supra to produce recombinant adenoviruses. In the viral context, expression of inserted genes is driven by the adenovirus E3 promoter.

Recombinant viruses that are both E1 and E3 deleted are generated by a double homologous recombination procedure for E1-replacement vectors using a plasmid-based system consisting of:

an adapter plasmid for E1 replacement according to the invention, with or without insertion of a first gene of interest, the pWE/Ad.AflII-EcoRI fragment, and the pBr/Ad.Bam-rITRΔgp19K plasmid with or without insertion of a second gene of interest.

In addition to manipulations in the E3 region, changes of (parts of) the E4 region can be accomplished easily in pBr/Ad.Bam-rITR. Moreover, combinations of manipulations in the E3 and/or E2A and/or E4 region can be made. Generation and propagation of such vectors, however, demands packaging cell lines that complement for E2A and/or E4 in trans.

Example 6

Angiogenesis Assay

Human foreskin microvascular endothelial cells (MVEC) were grown to confluency in M199 medium supplemented with 10% human serum (HS), 10% new-born calf serum (NBCS), penicillin and streptomycin and infected with $3.10\_$ pfu/ml Ad.IG.CMV.eNOS for 1 hour in M199 +2% NBCS. Medium was refreshed and cells were incubated overnight in M199+10% HS+10% NBCS.

Angiogenesis was analysed as described in Koolwijk et al. J. Cell Biol. 132 p1177–1188 (1996). Briefly, highly confluent MVEC were detached, seeded in a 1.25:1 split ratio on human fibrin matrices as cultures consisting either of uninfected cells, 100% infected cells or mixed cultures consisting of 10% infected/90% uninfected cells and cultured in M199 medium supplemented with 10% human serum (HS), 10% new-born calf serum (NBCS), penicillin and streptomycin.

Invading cells and the formation of tubular structures of endothelial cells in the three-dimensional fibrin matrix were analysed by phase contrast microscopy. After 7 days the total length of the tube-like structure of six randomly chosen microscopic fields per well (7.3 mm$^2$/field=43.8% of the total well) was measured using a Nikon FXA microscope equipped with a monochrome CCD camera (MX5) connected to a computer with Optimas image analysis software, and expressed as total tube length/cm$^2$.

Part of the Ad.IG.CMV.eNOS infected MVEC cells was used to analyse the NOS activity. NOS activity was analysed by measuring the conversion of L-$^1$_C-Arginine to L-$^1$_C-Citruline, the so-called citrulline assay.

For the angiogenesis experiments incubations are performed with cultures of uninfected cells, 10% infected MVEC and of 100% infected MVEC.

All incubations have been performed in the presence of 1 ng/ml TNF-α. Specific conditions tested in the presence and absence of virus were control, +bFGF: 5 ng/ml, +VEGF: 25 ng/ml, +bFGF+L-NAME: 5 ng/ml, 100 iM

Example 7

Effect of Adenoviruses on Angiogenesis

The NOS activity in Ad.IG.CMV.eNOS infected MVEC, expressed as dpm L-$^1$_C-citruline, was 3937 dpm versus 3703 dpm in uninfected MVEC, indicating that activity is present, but that this activity is not extremely high and might be improved.

Uninfected MVEC formed capillary-like structures in the fibrin matrices only after stimulation with the TNF-α in combination with bFGF or VEGF. Co-culturing with 10% Ad.IG.CMV.eNOS infected MVEC resulted in an enhanced tube formation, already visible after 5 days. Using cultures existing for 100% of infected cells resulted in less tube formation, probably due to effects of adenoviral infection on the invasive behaviour of these cells, as we have observed previously with other viruses.

After 7 days, the experiment was stopped, tube formation was analysed visually and quantified by image analysis (see FIG. 4).

Tube formation was clearly enhanced in the presence of 10% Ad.IG.CMV.eNOS infected MVEC, even in cultures stimulated only with TNF-α. The strongest induction, 2.1 fold, can be seen in the VEGF+TNF-α stimulated cultures. In the bFGF+TNF-α stimulated cultures a 1.65 fold induction by eNOS overexpression was observed. In the cultures existing for 100% of infected cells the tube formation, although present, is less pronounced than the 10% cultures when analysed by image analysis for total tube length. However, the number of starting sprouts is clearly increased in the 100% cultures. In the bFGF+TNF-α stimulated cultures it can be seen that addition of L-NAME (100 $\mu$M), an inhibitor of NOS activity, resulted in a small reduction of tube formation, not only in the presence of NOS infected cells but also under normal conditions. This might suggest that endogenous NOS activity is already involved in the process leading to tube formation. It can be concluded that infection with Ad.IG.CMV.eNOS has an enhancing effect on in vitro angiogenesis c.q. capillary-like tube information in fibrin matrices.

Figure 5:
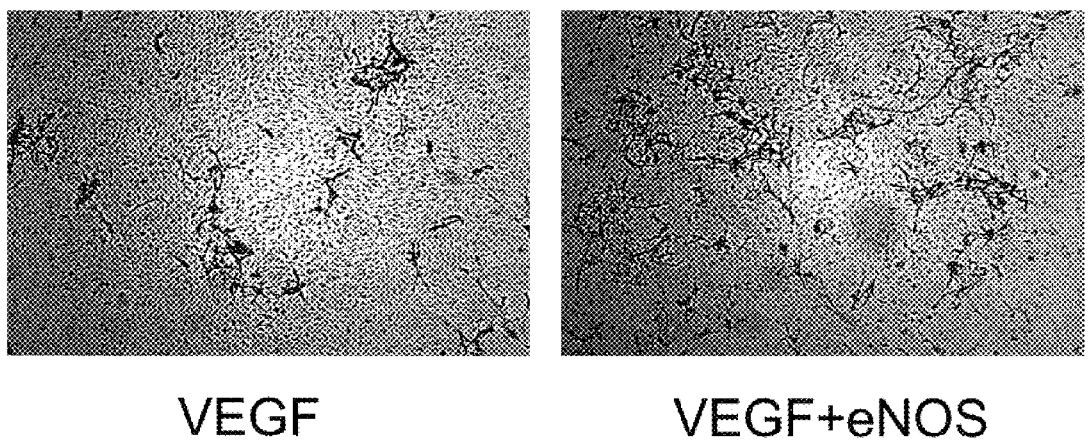
FIG. 5. Photographs of MVEC cells grown in the presence of VGEF with or without MVEC cells infected with Ad.IG.CMV.NOS.

Especially the enhancing effect on tube formation of eNOS overexpression in the VEGF stimulated cultures is very interesting, since the dose of VEGF used, 25 ng/ml, is known to give maximal induction of tube formation in the test system (FIG. 5).

Example 8

Improved Angiogenesis in Mice Following Administration of Ad.IG.CMV.eNOS.

A murine model of operatively induced hindlimb ischemia was used to investigate the impact of gene therapy to promote angiogenesis. Hindlimb ischemia was induced in 20 mice according to Murohara T et al (Murohara T., et al., 1998, J. Clin. Invest. 101, pp 2567–2578). Sixteen mice were divided into 4 groups of 4 mice which were injected with $10^6$, $10^7$, $10^8$, $10^9$ pfu Ad.IG.CMV.eNOS, respectively. Four mice received an injection with PBS and served as negative controls. Upon evaluation of the mice by laser Doppler flow analysis and capillary density measurement (Murohara T., et. al., 1998, J. Clin. Invest. 101, pp 2567–2578) we observed a dose dependent increase in angiogenesis compared to PBS injected control mice.

CITED LITERATURE

Nitric oxide synthase modulates angiogenesis in response to tissue ischemia. Murohara T, Asahara T, Silver M, Bauters C, Masuda H, Kalka C, Kearney M, Chen D, Symes J F, Fishman M C, Huang P L, Isner J M J Clin Invest Jun. 1, 1998; 101 (11); 2567–78

Co-operative effect of TNF-α, bFGF, and VEGF on the formation if tubular structures of human microvascular endothelial cells in a fibrin matrix. Role of urokinase activity. Koolwijk P, Van Erck M G M, de Vree W J A, Vermeer M A, Weich H A, Hanemaaijer R, Van Hinsbergh V V M, J. Cell Biol. 132 p1177–1188 (1996).

Vascular endothelial growth factor-C (VEGF-C/VEGF-2) promotes angiogenesis in the setting of tissue ischemia. Witzenbichler B, Asahara T, Murohara T, Silver M, Spyridopoulos I, Magner M, Principe N, Kearney M, Hu J S, Isner J M, Am J Pathol August 1998; 153 (2): 381–94

Nitric oxide production contributes to the angiogenic properties of vascular endothelial growth factor in human endothelial cells. Papapetropoulos A, Garcia-Cardena G, Madri J A, Sessa W C J Clin Invest Dec. 15, 1997; 100 (12): 3131–9

Role of nitric oxide in the angiogenic response in vitro to basic fibroblast growth factor. Babaei S, Teichert-Kuliszewska K, Monge J C, Mohamed F, Bendeck M P, Stewart D J Circ Res May 18, 1998; 82 (9): 1007–15

Role of nitric oxide in angiogenesis and tumor progression in head and neck cancer. Gallo O, Masini E, Morbidelli L, Franchi A, Fini-Storchi I, Vergari W A, Ziche M J Natl Cancer Inst Apr. 15, 1998; 90 (8): 587-96

Nitric oxide is an upstream signal of vascular endothelial growth factor-induced extracellular signal-regulated kinase1/2 activation in postcapillary endothelium. Parenti A, Morbidelli L, Cui X L, Douglas J G, Hood J D, Granger H J, Ledda F, Ziche M J Biol Chem Feb. 13, 1998; 273 (7): 4220–6

Nitric oxide synthase lies downstream from vascular endothelial growth factor-induced but not basic fibroblast growth factor-induced angiogenesis, Ziche M, Morbidelli L, Choudhuri R, Zhang H T, Donnini S, Granger H J, Bicknell R J Clin Invest Jun. 1, 1997; 99 (11): 2625–34

TABLE 1

Number of colonies after transfection of PER.C6 with E2A expression vectors:

| plasmid | number of colonies | cell lines established |
| --- | --- | --- |
| pcDNA3 | ~200 | 4/4 |
| PcDNA3wtE2A | 4 | 1/4 |
| PcDNA3tsE2A | ~100 | 37/45 |

TABLE 2

C3-9 and pareutal PE#.bjnfection with d1802 (Ad2 deleted in E2A gene) or IG.Ad.CMVeLaCZ at 32° C.

| cell line infected | CPE with IG.Ad.CMV.LacZ | CPE with d1802 |
| --- | --- | --- |
| PER.C6 | + | − |
| PER.C6.ts125E2A | + | + |

What is claimed is:

1. A method for enhancing and/or inducing collateral blood vessel formation in an individual comprising:
   directly administering to the individual's ischemic muscle tissue a nucleic acid delivery vehicle comprising:
   a nucleic acid comprising at least on DNA sequence encoding for an nitric oxide synthase operatively linked to a promoter, and
   a nucleic acid delivery carrier,
   wherein expression of said DNA sequence results in collateral blood vessel formation.

2. The method according to claim 1, wherein said nucleic acid delivery vehicle further comprises at least one other DNA sequence encoding an additional collateral blood vessel formation promoting factor operatively linked to a promoter.

3. The method according to claim 1, wherein said promoter is an inducible promoter.

4. The method according to claim 2, wherein said promoter is a hypoxia inducible promoter.

5. The method of claim 1, wherein said muscle tissue is not in direct contact with blood under normal circumstances.

6. A system for the production of a nucleic acid delivery vehicle for enhancing and/or inducing collateral blood vessel formation, the system comprising:
   a plasmid comprising a nucleic acid comprising at least on DNA sequence encoding for an nitric oxide synthase operatively linked to a promoter and at least one DNA sequence encoding an additional collateral blood vessel formation promoting factor operatively linked to a promoter, and further comprising a nucleic acid delivery carrier wherein said nucleic acid delivery carrier comprises a virus vector selected from the group consisting of an adenovirus vector and an adeno-associated virus vector; and
   a packaging cell adapted for the production of said virus vector in the absence of replication competent adenovirus and adeno-associated virus vectors.

7. The system according to claim 3, wherein said packaging cell expresses at least one nucleic acid sequence integrated and another nucleic acid not integrated into chromosomal DNA of said packaging cell, wherein the integrated and non-integrated nucleic acids do not comprises sequence overlap, and wherein replication competent adenovirus are formed.

8. The system according to claim 4, wherein said integrated nucleic acid comprises at least an adenovirus E1-region, or a fragment of an adenovirus E1-region that possess adenovirus E1 activity.

9. The system according to claim 4, wherein said integrated nucleic acid comprises at least a sequence encoding adenovirus ts125 E2A protein, or a fragment thereof possess adenovirus E2A-protein activity.

10. The system according to claim 4, wherein said integrated nucleic acid comprises at least an adenovirus E4-region, or a fragment of an adenovirus E4-region that possess the adenovirus E4 activity.

11. The system according to claim 3, wherein said packaging cell a Per.C6 cell (ECACC deposit number 96022940).

* * * * *

UNITED STATES PATENT AND TRADEMARK OFFICE
CERTIFICATE OF CORRECTION

PATENT NO.    : 6,447,768 B1
DATED         : September 10, 2002
INVENTOR(S)   : Anton Jan van Zonneveld and Stefan Frederick Franciscus Verlingen It is certified that error appears in the above-identified patent and that said Letters Patent is hereby corrected as shown below:

Column 4,
Line 8, change "revered" to -- reversed --
Line 27, change "adneo-associated" to -- adeno-associated --
Line 56, change "along" to -- alone --

Column 6,
Line 3, change "C-b 3'" to -- C-3' --
Line 10, change "this" to -- This --
Line 22, change "LINEraized" to -- LINEarized --

Column 7,
Line 9, change "582 C" to -- 58º C --
Line 17, change "(50' to 3')" to -- (5' to 3') --
Line 29, before "PCR" change "the" to -- The --

Column 9,
Line 47, change "E2deletion" to -- E2A deletion --

Column 10,
Line 36, after "agarose" change "enzyme" to -- gel --
Line 54, after "adenovirus" insert -- insert --

Column 11,
Line 13, change "-30')" to -- -3') --
Line 48, change "("150 bp)" to -- (~150 bp) --

Column 14,
Line 52, insert an empty line before and after the subheading "Generation of adapter plasmids pAdMire and pAdApt"

Column 15,
Line 39, insert an empty line before and after the subheading "Generation of pAdApt-ceNOS"

Column 16,
Line 19, change "−25" to -- ~25 --
Line 19, change "−80%" to -- ~80% --
Line 26, change "−50%" to -- ~50% --
Line 29, change "−80%" to -- ~80 --

UNITED STATES PATENT AND TRADEMARK OFFICE
CERTIFICATE OF CORRECTION

PATENT NO. : 6,447,768 B1
DATED : September 10, 2002
INVENTOR(S) : Anton Jan van Zonneveld and Stefan Frederick Franciscus Verlingen It is certified that error appears in the above-identified patent and that said Letters Patent is hereby corrected as shown below:

Column 31,
Line 5, before "nitric" change "an" to -- a --
Line 26, change "on" to -- one --

Column 32,
Line 5, change "comprises" to -- comprise --
Line 2, after "cell" and before "a" insert -- is --

Signed and Sealed this

Twenty-second Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.  : 6,447,768 B1  Page 1 of 1
DATED       : September 10, 2002
INVENTOR(S) : Anton Jan van Zonneveld and Stefan Frederik Franciscus Verlinden It is certified that error appears in the above-identified patent and that said Letters Patent is hereby corrected as shown below:

Title page,
Item [75], Inventors, change "Verlingen" to -- Verlinden --

Column 32,
Lines 8 and 27, change "claim 3" to -- claim 6 --
Lines 15, 19 and 23, change "claim 4" to -- claim 7 --

Signed and Sealed this

Twenty-third Day of September, 2003

JAMES E. ROGAN
*Director of the United States Patent and Trademark Office*